(12) United States Patent
Hensler

(10) Patent No.: US 11,458,030 B2
(45) Date of Patent: *Oct. 4, 2022

(54) BONE INFUSION APPARATUS AND METHODS FOR IN INTERBODY GRAFTS

(71) Applicant: H & M INNOVATIONS, LLC, Wilmington, NC (US)

(72) Inventor: Robert Sean Hensler, Wilmington, NC (US)

(73) Assignee: H&M INNOVATIONS, LLC, Wilmington, NC (US)

(*) Notice: Subject to any disclaimer, the term of this patent is extended or adjusted under 35 U.S.C. 154(b) by 436 days.

This patent is subject to a terminal disclaimer.

(21) Appl. No.: 16/505,675

(22) Filed: Jul. 8, 2019

(65) Prior Publication Data

US 2019/0343659 A1    Nov. 14, 2019

Related U.S. Application Data

(60) Continuation of application No. 15/583,810, filed on May 1, 2017, now Pat. No. 10,342,679, which is a
(Continued)

(51) Int. Cl.
*A61F 2/46* (2006.01)
*A61F 2/44* (2006.01)
(Continued)

(52) U.S. Cl.
CPC .......... *A61F 2/4644* (2013.01); *A61F 2/0095* (2013.01); *A61F 2/28* (2013.01); *A61F 2/44* (2013.01); *A61F 2/4455* (2013.01); *A61F 2/46* (2013.01); *A61F 2/4601* (2013.01); *B65D 25/10* (2013.01); *B65D 51/24* (2013.01); *B65D 51/26* (2013.01)

(58) Field of Classification Search
None
See application file for complete search history.

(56) References Cited

U.S. PATENT DOCUMENTS 2,466,407 A * 4/1949 Ragnar ................. B29C 43/00
425/62
7,955,335 B2 * 6/2011 Gil ........................ A61F 2/4644
606/79
(Continued)

*Primary Examiner* — Tessa M Matthews
(74) *Attorney, Agent, or Firm* — Chad D. Tillman; Tillman Wright, PLLC

(57) ABSTRACT

A bone infusion apparatus for interbody grafts includes a container; a retainer, the retainer including a recess for receiving therein bone graft material; and a lid including a plunger assembly. A method of preparing bone including cadaver bone for use in cervical fusion includes: placing cadaver bone combined with bone collected from a patient into a recess of the retainer; placing the retainer in the container; filling the container with a liquid; attaching a lid the container; depressing a plunger of the lid such that a press head advances toward the retainer causing a dynamic pressure to act on the cadaver bone combined with the bone collected from the patient; suctioning the liquid from the container; removing the combined bone from the retainer; and placing the combined bone removed from the container into a vertebral interspace of the patient.

12 Claims, 10 Drawing Sheets

Related U.S. Application Data continuation of application No. 14/713,923, filed on May 15, 2015, now Pat. No. 9,636,235, which is a division of application No. 13/831,533, filed on Mar. 14, 2013, now Pat. No. 9,034,044.

(60) Provisional application No. 61/700,639, filed on Sep. 13, 2012.

(51) Int. Cl.
| | |
|---|---|
| *A61F 2/00* | (2006.01) |
| *A61F 2/28* | (2006.01) |
| *B65D 25/10* | (2006.01) |
| *B65D 51/24* | (2006.01) |
| *B65D 51/26* | (2006.01) |

(56) References Cited

U.S. PATENT DOCUMENTS

| | | | |
|---|---|---|---|
| 8,845,605 B2* | 9/2014 | Hensler | A61M 1/0001 |
| | | | 604/319 |
| 10,085,816 B2* | 10/2018 | Starkey | A61B 17/1635 |
| 2008/0214998 A1* | 9/2008 | Kurek | A61F 2/4601 |
| | | | 604/93.01 |
| 2008/0217264 A1* | 9/2008 | Leach | B01L 3/5021 |
| | | | 210/512.1 |
| 2020/0047954 A1* | 2/2020 | Giovannetti | A24F 15/20 |
| 2021/0113351 A1* | 4/2021 | Lambarth | A61M 1/79 |
| 2021/0236302 A1* | 8/2021 | Kim | A61B 17/1635 |

\* cited by examiner

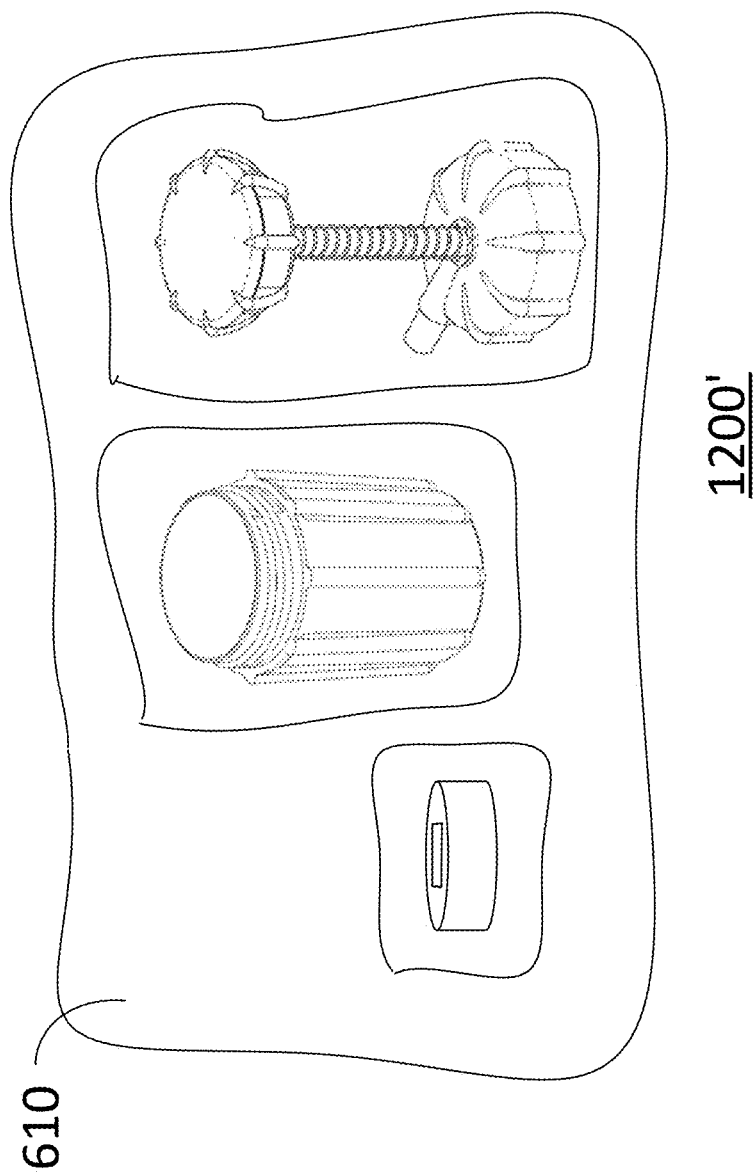

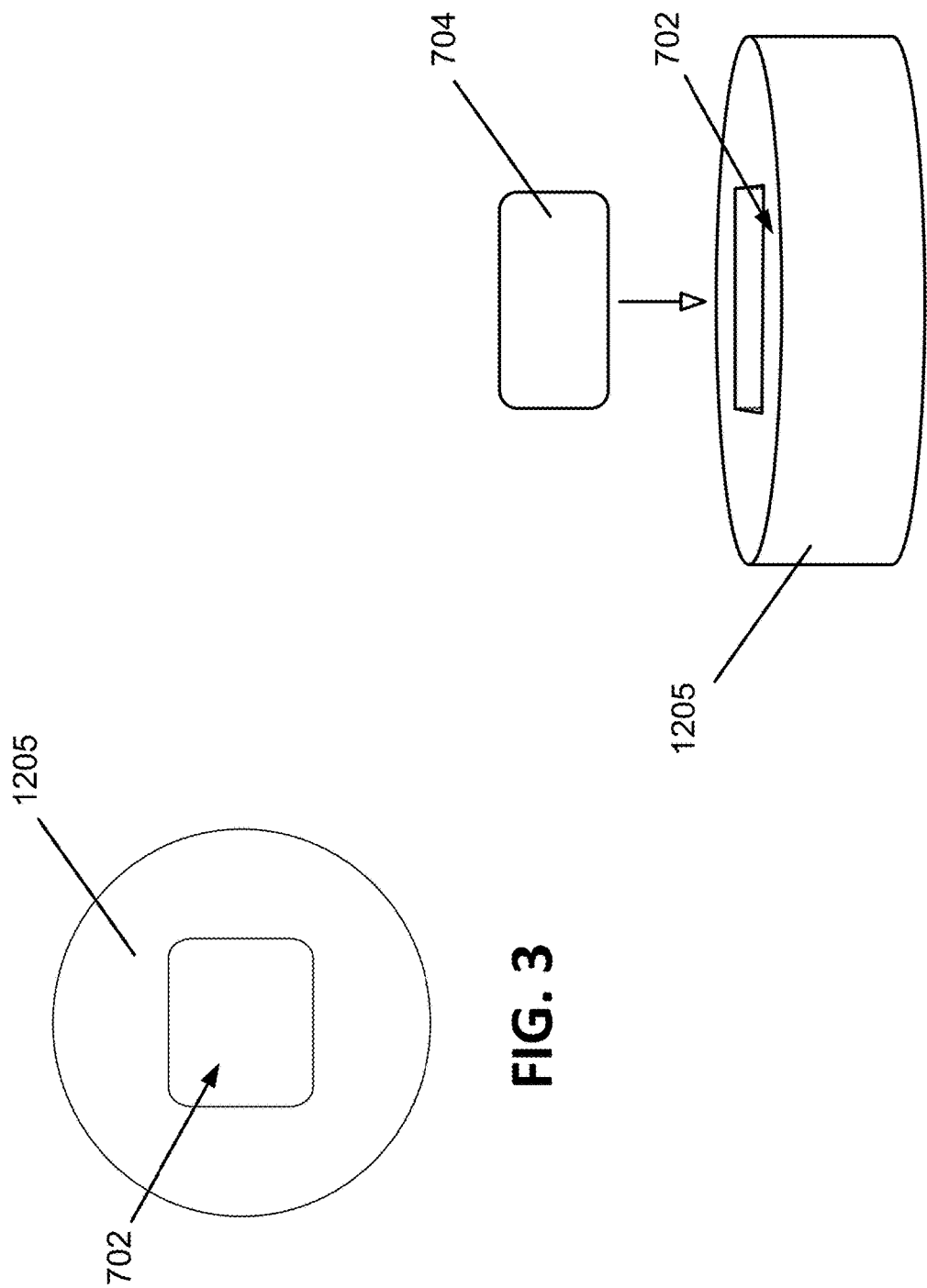

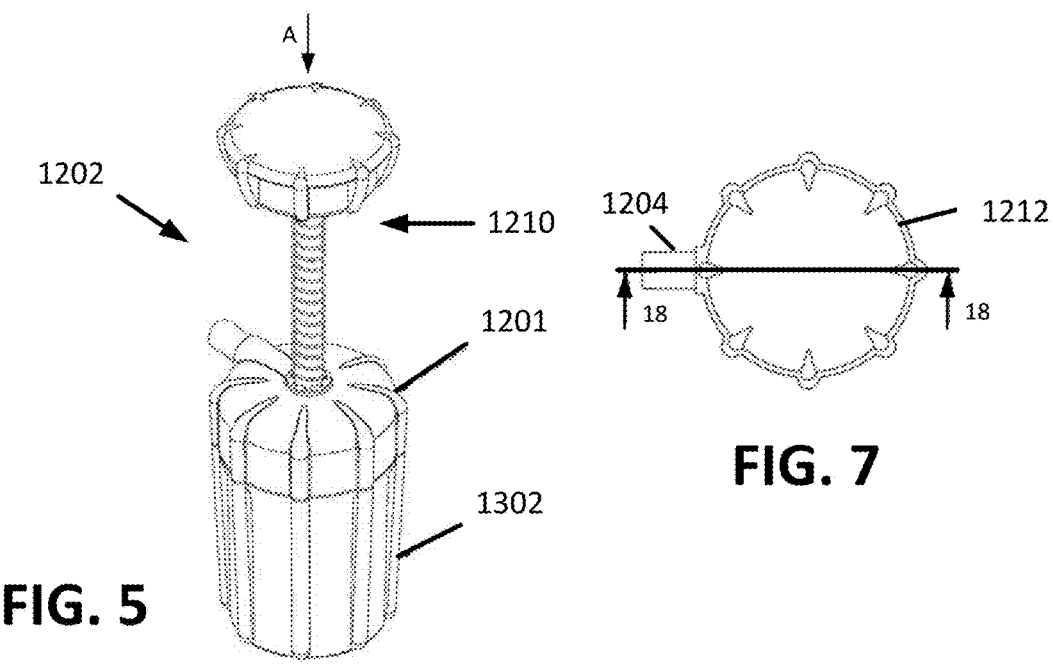
FIG. 5
FIG. 7
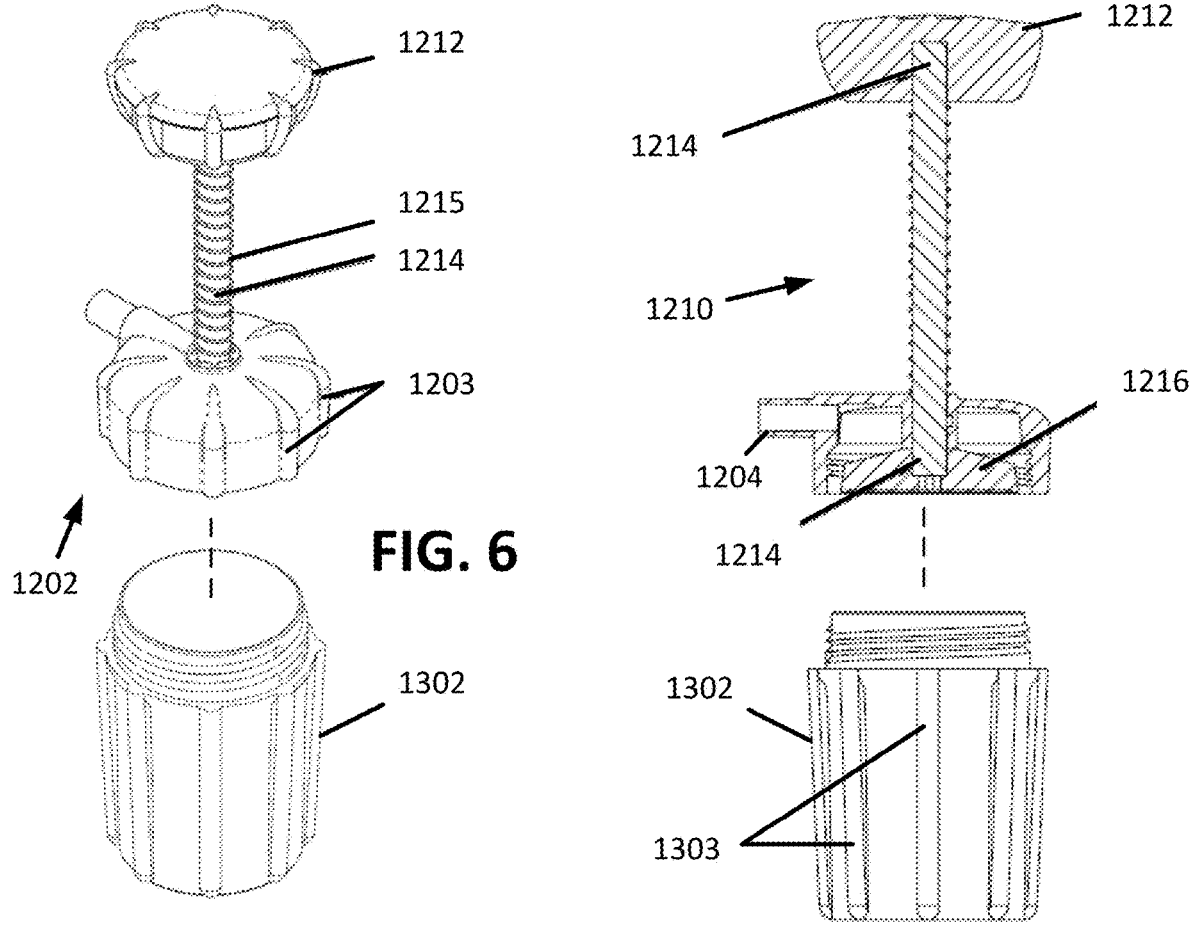
FIG. 6
FIG. 8

BONE INFUSION APPARATUS AND METHODS FOR IN INTERBODY GRAFTS

CROSS-REFERENCE TO RELATED APPLICATIONS

This application is a continuation of, and claims priority under 35 U.S.C. § 120 to, U.S. patent application Ser. No. 15/583,810, now U.S. Pat. No. 10,342,679, which '810 application is a continuation of, and claims priority under § 120 to, U.S. patent application Ser. No. 14/713,923, now U.S. Pat. No. 9,636,235, which '923 application is a divisional application of, and claims priority under § 120 and § 121 to, U.S. patent application Ser. No. 13/831,533, now U.S. Pat. No. 9,034,044, which '533 application is incorporated by reference herein, and which '533 application is a nonprovisional of, and claims priority under 35 U.S.C. § 119(e) to, provisional U.S. patent application 61/700,639, filed Sep. 13, 2012, which provisional patent application is incorporated by reference herein. A copy of the disclosure of this provisional application is contained in the Appendix, which is incorporated herein by reference. This application also incorporates herein by reference each of U.S. patent application publication nos. 2012/0279933 and 2012/0330220.

BACKGROUND

Various embodiments of bone and tissue collection assemblies are disclosed in the incorporated references and, with particular regard to such collection assemblies that are used to collect bone, each is generally referred to herein as a "bone press". In accordance with these incorporated references, a preferred bone press includes two containers and two lids that are interchangeable with the containers. One of the lids includes two ports, and the other lid includes a plunger assembly. The bone press separates blood from bone rapidly and effectively, with the bone being collected in a first stage with a container and the first lid with the two ports, and with the bone being separated from the aspirated fluid in a second stage with the same container and the other lid with the plunger assembly via a manual pressing action. While the bone is separated from the aspirated fluid, additional aspirated fluid can be captured using the other container with the first lid. Patient-specific bone that is thereby collected can be used in multiple surgical applications pertaining to the fusion of bone. As used herein, a "bone press" is intended to comprise at least one container and the two lids, but preferably further includes an additional container for improved efficiency in collecting the aspirated fluid.

In one such surgical application, bone is collected after high speed drilling for placing within a graft between two or more vertebral interspaces. Single or multi-level cervical fusions incorporate such interbody grafts. It is also known that grafts can be made of specialized polymers or cadaver bone. The cadaver bone graft is demineralized bone and does not have the ability to fuse on its own. Thus, additional bone must be used that, preferably, is taken from a patient using a bone press.

One or more embodiments of the present disclosure are believed to represent improvements and enhancements to surgical procedures in which cadaver bone is combined with bone collected from a patient and subsequently inserted into the patient.

SUMMARY

The present disclosure includes many aspects and features.

In one aspect, a bone infusion apparatus for interbody grafts comprises: a bone press; and a retainer, the retainer including a recess for receiving therein bone graft material.

In a feature of this aspect, the retainer is resilient and compressible.

In another feature, the retainer is resilient and compressible.

In another feature, the retainer is made of rubber.

In another feature, the recess of the retainer if located in a top surface of the retainer.

In another feature, a profile of the retainer matches an inner surface profile of the container.

In another feature, the retainer is positionable within the container in a frictional fit and/or forms a fluid seal with the inner surface of the container.

In another feature, the retainer consumes the space of the container proximate a bottom of the container and forms an elevated floor of the interior space of the container.

In another feature, score lines or other areas of weakened integrity are provided in the retainer for increasing the perimeter of the recess; increasing the depth of the recess; or both.

In another feature, comprising one or more spacers for consuming a bottom portion of the space within the recess of the retainer by which the depth of the recess of the retainer is adjusted.

In another feature, a spacer has the same profile as the recess and wherein the spacer is made of rubber or equivalent material.

In another feature, the retainer is in the shape of a hockey puck or is otherwise disc-shaped.

In another feature, the bone press comprises a container and first and second lids, the first lid comprising a plunger assembly and the second lid comprising first and second ports, the first and second lids each being configured for attachment to the container whereby the lids are interchangeable with respect to the container.

In another feature, the bone press further comprises an additional container on which the first and second lids each are configured for attachment whereby the lids are interchangeable with respect to the additional container, and wherein the retainer is configured for disposition within the container when the lid comprising the plunger assembly is attached to the additional container.

In another aspect, a bone infusion apparatus for interbody grafts comprises: a container; a retainer, the retainer including a recess for receiving therein bone graft material; and a retainer. The retainer is configured for disposition within the container when the lid is attached to the container.

In another aspect, a method of preparing bone including cadaver bone for use in cervical fusion, comprising the steps of: placing cadaver bone combined with bone collected from a patient into a recess of a retainer; placing the retainer in a container; filling the container with a liquid; attaching a lid the container; depressing a plunger of the lid such that a press head advances toward the retainer causing a dynamic pressure to act on the cadaver bone combined with the bone collected from the patient; suctioning the liquid from the container; removing the combined bone from the retainer; and placing the combined bone removed from the container into a vertebral interspace of the patient.

In a feature, the method further comprises repeating step (e).

In another feature, the liquid with which the container is filled comprises blood; saline; or a combination thereof.

In a feature, the method further comprises the step of soaking the combined bone in the liquid for a period of time before commencing pressing.

In a feature, the method further comprises, as a preliminary step, collecting the bone from the patient using a bone press. The container and the lid preferably are utilized in this respect as they preferably form components of the bone press.

In another feature, said step (f) comprises attaching suction to a port of the lid.

In another feature, said step (e) comprises depressing the plunger causing the press head to advance into abutment with retainer.

In another feature, said step (e) further comprises depressing the plunger until a press head abuts the cadaver bone combined with the patient's bone.

In another feature, the retainer is resilient and compressible.

In another feature, the retainer is made of rubber.

In another aspect, a retainer for use with a container and lid of a bone press comprises puck shaped body having a recess within which bone material is placed. The recess preferably is located in a top surface of the body. The dimensions of the recess preferably are 15 mm in width by 15 mm in length by 12 mm in height. Moreover, the body preferably is formed from a surgical grade rubber or other material that is compressible and resilient.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

FIG. 2 schematically illustrates an alternative kit in accordance with one or more preferred embodiments.

FIG. 3 schematically illustrates a top plan view of a puck or disc-shaped retainer in accordance with one or more embodiments.

FIG. 4 schematically illustrates a side view of the retainer of FIG. 3 wherein bone is being placed into a top recess of the retainer.

FIG. 5 schematically illustrates a lid attached to a container in accordance with one or more embodiments.

FIG. 6 schematically illustrates in partial exploded view the lid and container of FIG. 5.

FIG. 7 schematically illustrates a top plan view of the handle of the plunger of the lid of FIGS. 5 and 6:

FIG. 8 schematically illustrates an exploded, side plan view of the lid and container of FIG. 6, wherein the lid is shown in partial cross-section taken along the line 18-18 of FIG. 7.

DESCRIPTION

Figure 1:
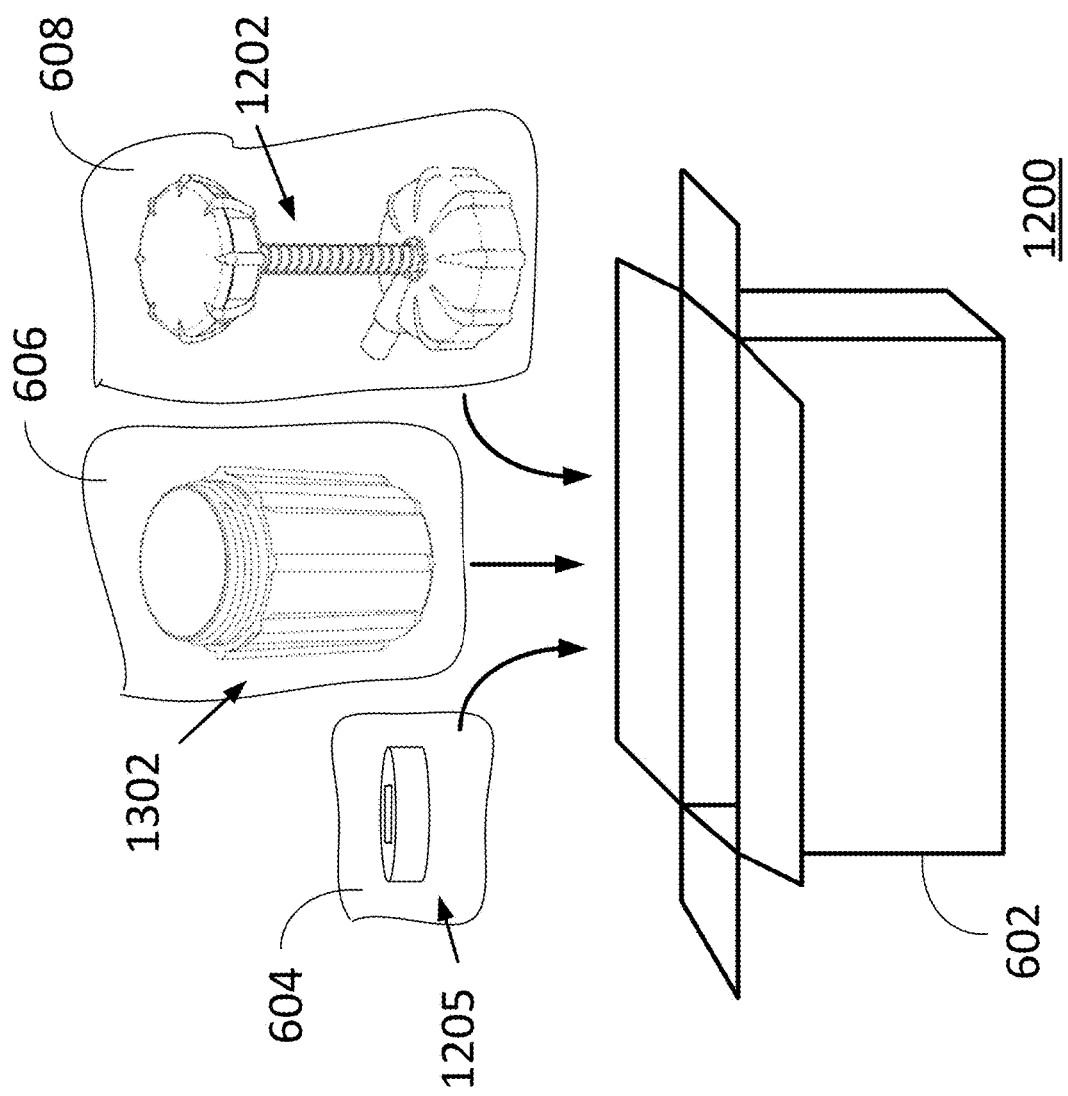
FIG. 1 schematically illustrates a kit in accordance with one or more preferred embodiments.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a fill and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." in contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In accordance with preferred embodiments of the present disclosure, a retainer is provided for use preferably with a container and lid of a bone press, wherein the lid includes a plunger assembly. These components of a bone press are used with the retainer to infuse patient-specific bone cells collected using a bone press within the porous trabecular network of cadaver bone. Specifically, the container and lid including a plunger assembly with press head, is used to infuse the bone with the cadaver bone. Moreover, the entire bone press preferably is used if the autologous bone is to be collected first; or only a container and a lid with the plunger assembly of the bone press are utilized where the bone to be infused is obtained through other means.

The retainer preferably is disc shaped and includes a recess within which bone material is placed. The retainer preferably is made from a surgical grade rubber, and it is believed that the retainer facilitates coalescence of the autologous bone and the cadaver bone. The coalesced bone material then can be inserted into the patient. Like a bone press of the incorporated references, the retainer preferably is a single-use, disposable item. Use of a disposable retainer avoids the potential of infection from reuse.

It is believed that using a retainer made of rubber, or other similar inert material with similar characteristics of compressibility and resilience, will allow for multiple cadaver bone grafts sizes, in that the rubber retainer will allow for compressibility and easy removal of the graft after infusion pressure during the press stage. Moreover, it is contemplated that a larger recess can be cut out of the rubber retainer, if desired. In this respect, score lines or other areas of weakened integrity can be provided for increasing the perimeter of the recess; the depth of the recess; or both. It is also contemplated that one or more spacers can be used to adjust the height of the recess, if desired. Such spacers preferably have the same profile as the recess and also are made of rubber or comparable material, like the retainer.

Turning now to the drawings, a contemplated kit 1200 in accordance with one or more preferred embodiments is shown in FIG. 1. The kit 1200 includes a retainer 1205; a container 1302; and a lid 1202 having a plunger assembly. The lid and plunger assembly thereof are described in more detail below with reference to FIGS. 5-12.

Preferably, each component is contained in its respective own sterile bag 604,606,608, and each component may be vacuum-packed within its own respective bag. Additionally, the components are contained within a master container of the kit, which container is shown as comprising a box 602 in FIG. 1. An alternative kit 1200' is shown in FIG. 2, wherein the master container comprises a bag 610 instead of the box 602. Otherwise, the kit 1200' of FIG. 2 is intended to be the same as the kit 1200 of FIG. 1. Furthermore, the components of the kit 1200' may be vacuum-packaged within their own respective bags within the bag 610.

A top plan view of the retainer 1205 in accordance with one or more embodiments is schematically shown in FIG. 3. The retainer 1205 includes a centrally located recess 702 in which a bone graft is received. A side view of the retainer 1205 receiving a bone graft 704 is schematically illustrated in FIG. 4.

The container 1302 and lid 1202 with plunger assembly, including a press head, are disclosed and described with respect to FIGS. 5-12 and 17-19. In particular, FIG. 5 schematically illustrates the lid 1202 attached to the container 1302. The lid 1202 includes a screw-on top 1201 and a plunger assembly. Moreover, while a screw-on engagement is preferred, other engagements are contemplated, such as a snap-fit engagement between the lid and container.

The plunger assembly comprises a plunger 1210 that is biased into and disposed in a first position as shown in FIG. 5. As perhaps best shown in FIG. 8, the plunger 1210 comprises a handle 1212, a shaft 1214, and a press head 1216. The plunger assembly further includes a spring 1215 that is generally coaxial with the shaft 1214 and that extends between the handle 1212 and the top 1201. The spring 1215 biases the plunger 1210 into the first position as shown in FIG. 5, and acts against a downward force A that may be manually applied by hand to the handle 1212 in advancing the plunger 1210 from the first position toward a depressed, second position, in which the press head 1216 is located proximate a bottom of the container 1302.

The screw-on top 1201 includes a suction port 1204 that extends to a side of the top 1201, transversely to the shaft 1214 of the plunger 1210. The container 1302 is configured to receive the top 1201 in threading engagement, whereby the top 1201 is screwed onto the container 1302 and can be similarly screwed off of the container 1302.

The container 1302 preferably includes elongate protuberances or ribs 1303 that extend between the top and bottom of the container 1302 along the exterior surface thereof. The ribs 1303 preferably provide a good gripping surface for holding the container 1302 when screwing the top 1201 onto and off of the container 1302. Moreover, the top 1201 preferably includes ribs 1203 that also provide a good gripping surface. The ribs 1203 on the top 1201 preferably correspond to and align with the ribs 1303 on the container 1302 when the top 1201 is securely screwed onto the container 1302, thereby readily visually indicating that the top 1201 is tightly screwed onto the container 1302.

FIGS. 6 and 8 schematically illustrate the detachability of the lid 1202 and the container 1302. FIG. 7 schematically illustrates a top plan view of the lid 1202 detached from the container 1302; and FIG. 8 schematically illustrates a side plan view of the lid 1202 and container 1302 of FIG. 6, including a cross-sectional view of the lid 1202 taken along the line 18-18 in FIG. 7.

Figure 9:
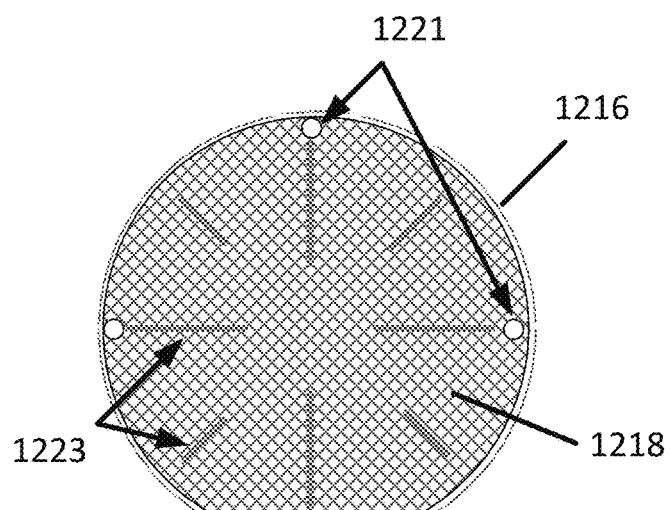
FIG. 9 schematically illustrates a plan view of the bottom of a press head of the plunger assembly of the lid of FIGS. 5-8, revealing a woven metal mesh or screen with a circular profile.

FIG. 9 schematically illustrates a plan view of the bottom of the press head 1216 and reveals a screen 1218 comprising a woven metal mesh. The screen 1218 preferably is secured to the press head 1216 in an injection molding process, with a circumferential portion of the press head 1216 being formed about a circumferential outer portion of the screen 1218 to thereby hold the screen 1218 within a recessed area on the underside of the press head 1216. In this respect, in at least one preferred embodiment the press head 1216 includes a lip of approximately 0.020 inches. In other embodiments, the screen 1218 may be glued or otherwise adhered to the press head, or secured using mechanical fasteners. Furthermore, the screen 1218 preferably includes four openings through which alignment protuberances or pins 1221 of the press head 1216 extend for alignment of the screen 1218 to the press head 1216. These pins 1221 further keep the screen 1218 from rotating about an axis of the press head 1216.

Additionally, the screen 1218 is supported by the press head 1216 as the plunger 1210 is moved through any contents in the container 1302 from the first position to the second position along the radially extending, elongate areas 1223 as indicated in FIG. 9. These areas comprise an alternating sequence of long and short radially extending, elongate areas 1223 spaced at equal intervals circumferentially about the screen 1218, and correspond to elongate, radially extending support members 1225 on the underside of the press head 1216. This support arrangement provides generally equally distributed support of the screen 1218 during advancement of the press head 1216.

Figure 10:
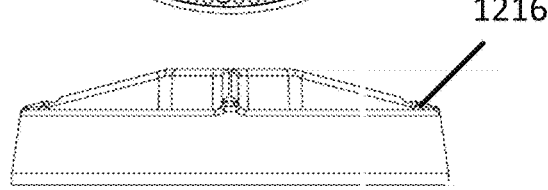
FIG. 10 schematically illustrates a side plan view of the press head of FIG. 9.
Figure 11:
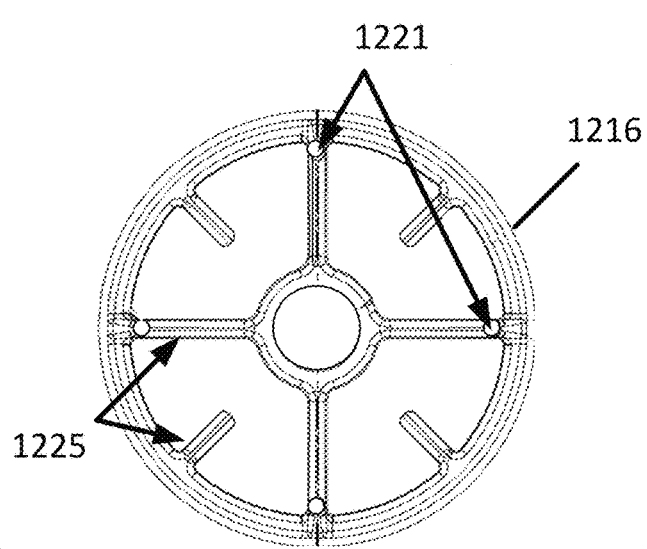
FIG. 11 schematically illustrates a plan view of the bottom of the press head of FIG. 9, wherein the screen is omitted.
Figure 12:
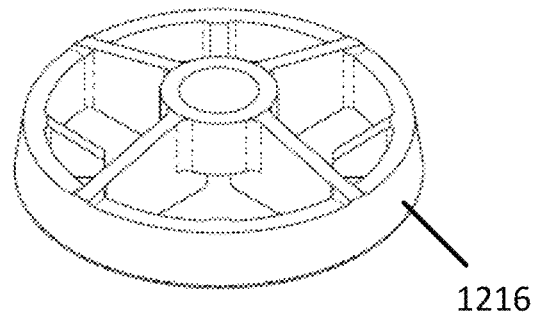
FIG. 12 schematically illustrates a perspective view of the press head of FIG. 11, wherein the screen is also omitted.

With further regard to the press head 1216 and omitting the screen 1218, FIG. 10 schematically illustrates a side plan view of the press head 1216; FIG. 11 schematically illustrates a top plan view of the press head 1216; and FIG. 12 schematically illustrates a perspective view of the press head 1216.

Figure 17:
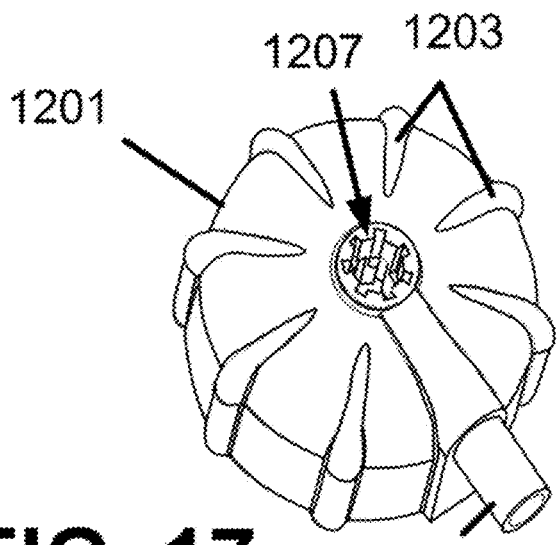
FIG. 17 schematically illustrates a perspective view of a screw-on top of the second lid of FIG. 8.
Figure 18:
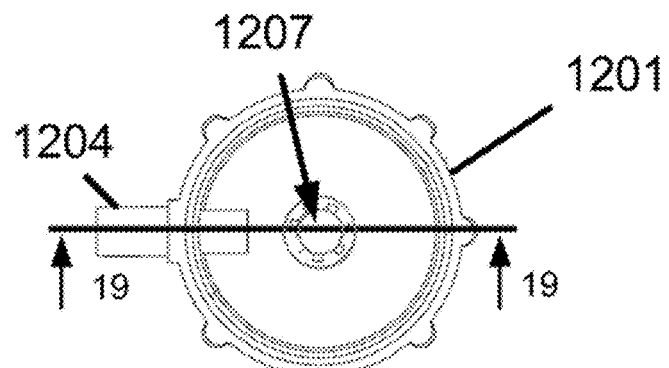
FIG. 18 schematically illustrates a bottom plan view of the screw-on top of FIG. 17.
Figure 19:
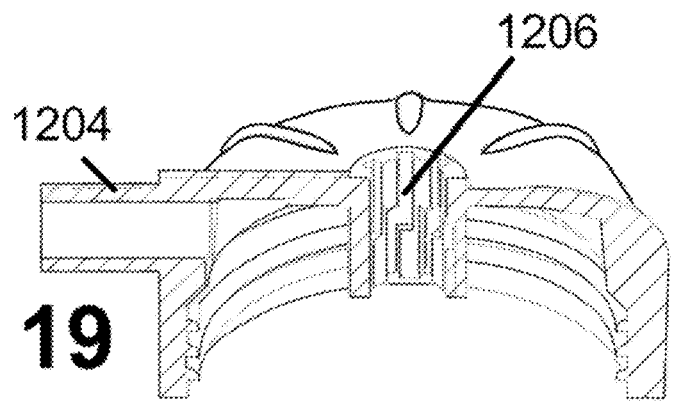
FIG. 19 schematically illustrates a perspective view of a cross-section of the screw-on top of FIG. 17 taken along the line 19-19 in FIG. 18.

Jumping now to FIGS. 17-19, FIG. 17 schematically illustrates a perspective view of the screw-on top 1201 of FIG. 8; FIG. 18 schematically illustrates a bottom plan view of the screw-on top 1201; and FIG. 19 schematically illustrates a perspective view of a cross-section of the screw-on top 1201 taken along the line 19-19 in FIG. 24. It will be seen from FIGS. 17-19 that the screw-on top 1201 defines passageways 1206 formed in the axial extent of the opening 1207 in the top 1201 through which the shaft 1214 of the plunger 1210 is received. Each of these passageways 1206 forms a vent when the shaft 1214 is received through the opening 1207. Furthermore, each passageway 1206 includes a top portion that is generally oriented in parallel to the axis of the opening 1207 and shaft 1214 when received therethrough; a middle portion that is generally circumferentially oriented to the axis of the opening 1207 and shaft 1214 when received therethrough; and a bottom portion that is generally oriented in parallel to the axis of the opening 1207 and shaft 1214 when received therethrough. The top portion and bottom portion of each passageway 1206 are thus offset from each other along the circumferential direction about the opening 1207. This is perhaps best seen in the passageway 1206 called out in FIG. 25.

Figure 13:
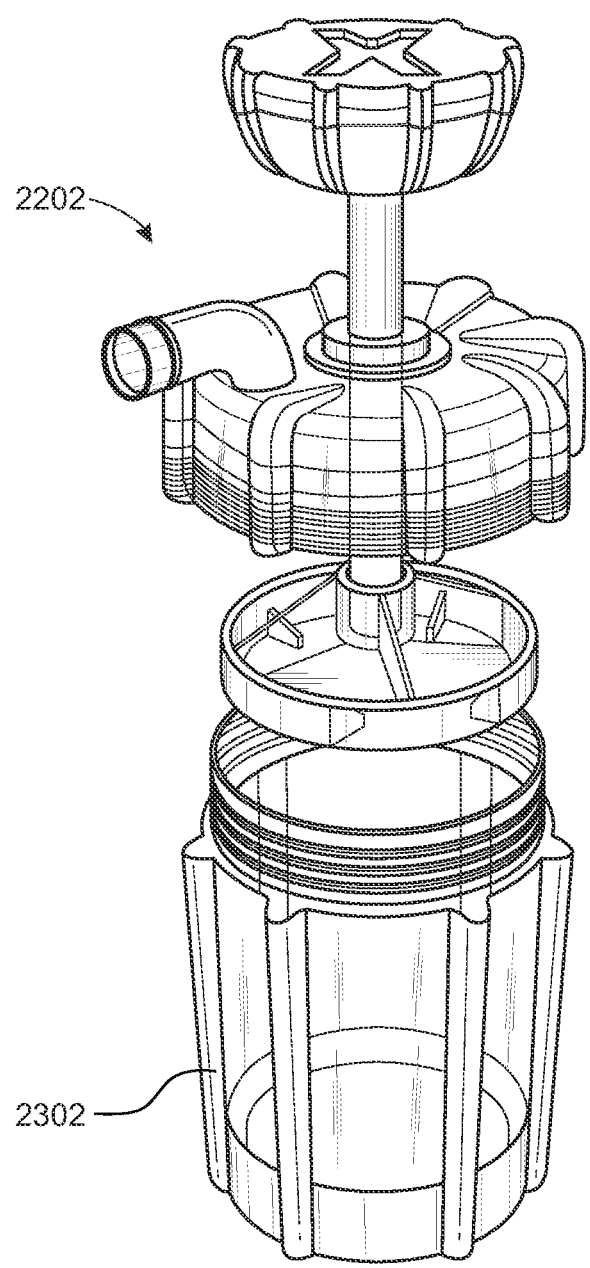
FIG. 13 illustrates in partial exploded view a rendering of a container and cover of a prospective commercial embodiment in accordance with one or more aspects and features of the present disclosure.

Returning now to FIG. 13, this drawing is a rendering of a container 2302 and a cover 2202 of two of the components of a prospective commercial embodiment of the present disclosure. The retainer is not shown in FIG. 13, which would further be part of the commercial embodiment.

Referring back to FIGS. 1-4, it will be appreciated that the retainer 1205 has been illustrated as being in the shape of a hockey puck or disc-shaped; however, the profile of the retainer 1205 preferably is designed to match a profile of the container in which it is placed so as to form a tight frictional fit and seal with the interior sides of the container. Moreover, the retainer preferably consumes a bottom portion of the container when in such position. It is recognized, however, that the retainer may in some embodiments have a peripheral profile that does not match the inside profile of the container and that a tight frictional fit and/or seal may not be formed. In such embodiments, the retainer may simply rest upon a bottom of the container other otherwise be supported.

The method is intended to be performed preferably by a surgical technologist at a sterile surgical table in the operating room. In use in accordance with preferred embodiments of the present disclosure, bone first is collected for infusing with the cadaver bone. It is preferred that autologous bone is collected using a bone press in accordance with the incorporated references. It is believed that by first using the bone press to obtain autologous bone, use of a hip marrow aspirate or other remote bone harvesting site can be avoided. Additionally, bone collected and ground into fine particles after use of a bone mill also can be used. Preceding events also may include removing a diseased disc at the location of the cervical fusion to be performed, including drilling, with use of the bone press for capturing autologous bone.

In any case, once obtained the bone is staged on the sterile surgical table in the operating room. The cadaver bone is placed on the surgical table. The collected bone, also known as bone dust or shavings, which is collected after use of a high speed drill or bone mill, is molded and inserted into the center conduit of the cadaver bone. The bone is molded and inserted through the center conduit of the cadaver bone preferably using tactile finger pressure. One or more center conduits typically exist in the cadaver bone in these type of grafts. Additional fine bone shavings further preferably are placed all around and into the cadaver bone, resulting in a thick layer or coating of bone shavings on the superior and inferior surfaces of the cadaver bone graft, which will have direct contact with the vertebral endplates one placed within the patient; this is believed to help optimize the infusion. Indeed it is believed that the fusion of autologous bone within the porous trabecular network of the cadaver bone, and the fusion of the upper and lower surfaces of the graft with the vertebrae once the graft has been inserted, will facilitate bone fusion and osteogenesis, as the demineralized cadaver bone requires live bone cells for fusion to occur.

The bone graft is then placed within the recess of the retainer, and the retainer is placed within a container of the bone press. Alternatively, the cadaver bone graft is placed in the recess of the disk after the retainer is placed in the container of the bone press. The recess in the retainer preferably is located proximate the center of the retainer. The bone graft is intended to be used for cervical fusions and, as such, the dimensions of the recess preferably are 15 mm in width by 15 mm in length by 12 mm in height. The bone graft is placed within the recess such that the center conduit extends in a generally parallel direction to the movement of the press head when the retainer is received within the container and the press head is advanced toward the retainer, as further described in the exemplary instructions detailed below.

Upon placement of the retainer and bone graft within the container, the container is filled with blood, saline, or a combination thereof, as desired and in accordance with surgeon preference; however, it is believed that the use of blood is optimal. Preferably the container is filled so that the fluid extends well above the top of the retainer when properly located within the container of the bone press.

The bone then may be allowed to soak within the fluid filled container, in accordance with surgeon preference, before performing the pressing action. Alternatively, soaking may be skipped and the pressing action may be employed following placement of the retainer and bone in proper position for the pressing action. It is preferred that, when hip marrow aspirate is used, the bone graft ordinarily be allowed to soak for about thirty minutes.

During any period of time for soaking, or when the pressing is to be performed, the lid having the plunger assembly is attached. In accordance with one or more preferred embodiments, the lid and container include opposing ribs that line up and register with each other when the lid is tightly screwed onto the container. Such visual indicators help to insure a proper fit.

Additionally, when pressing is to be performed, the suction is first attached to the side port on the lid. Then, using a steady downward motion, the press head is advanced to abutment with the retainer by manually depressing the plunger. Preferably, the press head then is further advanced until it abuts the top of the graft within the retainer. The press head is then released, and the press head is again advanced until it abuts the top of the graft. During or following pressing, the container is tilted in order to drain off the fluid within the container. Following pressing, the lid is removed from the container.

As a result of the pressing action from pressing down of the press head, the press head is advanced toward the retainer and it is believed that the dynamic fluid pressure created results in greater liquid lubrication of the bone cells in the bone matrix, causing the autologous bone to infuse into the porous trabecular network of the cadaver bone graft. It is further believed that the bone cells remain viable, with no material cell destruction resulting from the pressing action.

To obtain the graft, the container then is gently tilted in the middle of the sterile table so that the graft gently falls out onto the table or into one's hand. The titling should be done gently so that the graft does not fall onto the ground or bounce off of the table. Alternatively, the retainer is removed from the container and the graft is removed from the retainer. The retainer can be removed by placing the container upside down and tapping the container. An instrument can be used to dislodge the retainer from the container if needed. Once removed from the retainer, the bone graft is ready for placement into the interbody space as the surgeon deems appropriate.

The bone press can be utilized further to collect additional bone during the operation, if needed. Preferably, at the end of the surgery, the bone press and retainer are each discarded in accordance with applicable HAZMAT protocols.

Figure 14:
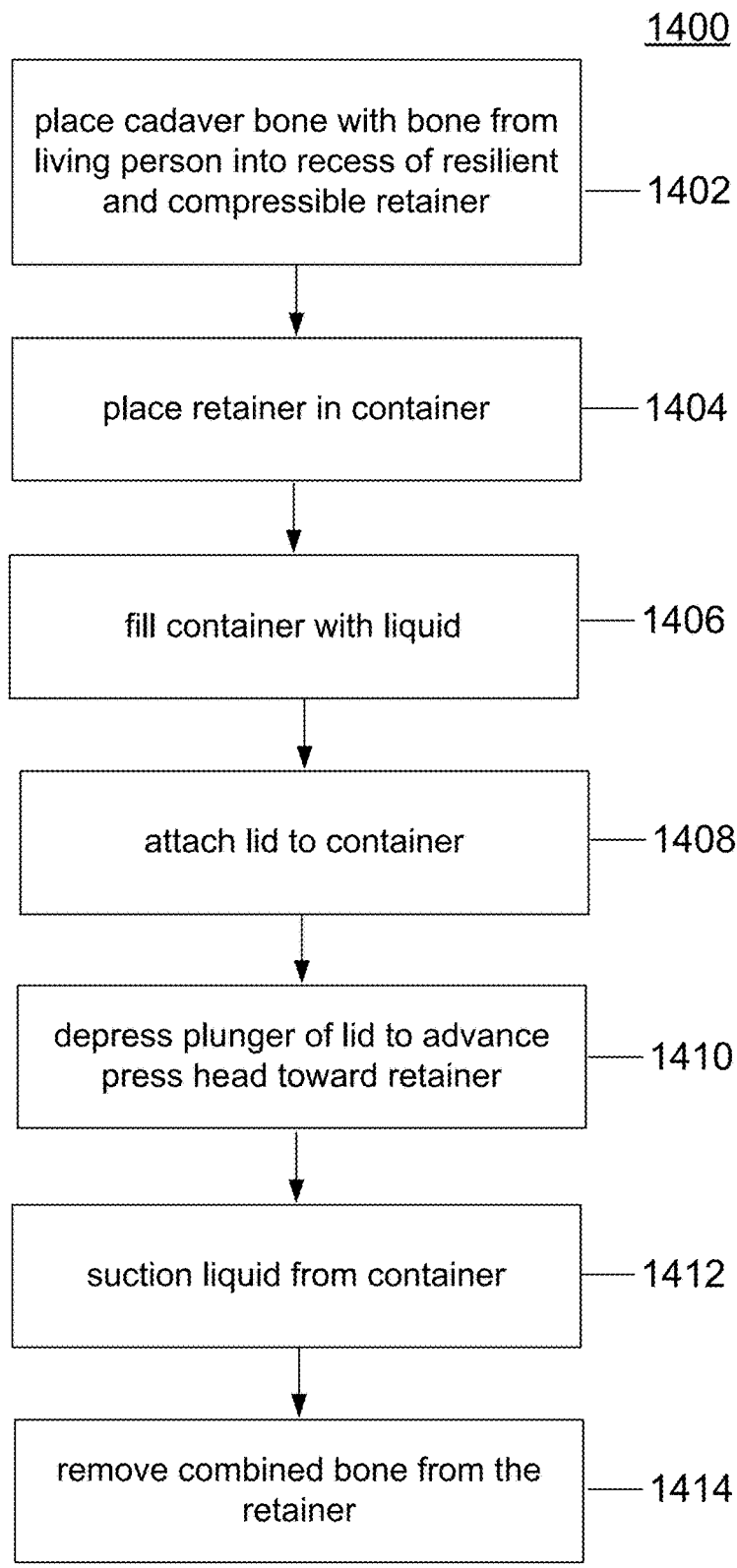
FIG. 14 illustrates a method in accordance with a preferred embodiment of the invention.

With reference to FIG. 14, a preferred method 1400 of preparing bone including cadaver bone for use in cervical fusion includes: (a) the step 1402 of placing cadaver bone combined with bone collected from a living person into a recess of a resilient and compressible retainer; (b) the step 1404 of placing the retainer in a container; (c) the step 1406 of filling the container with a liquid; (d) the step 1408 of attaching a lid to the container; (e) the step 1410 of depressing a plunger of the lid such that a press head advances toward the retainer causing a dynamic pressure to act on the cadaver bone combined with the bone collected from the living person; (0 the step 1412 of suctioning the liquid from the container; and (g) the step 1414 of removing the combined bone from the retainer.

Figure 15:
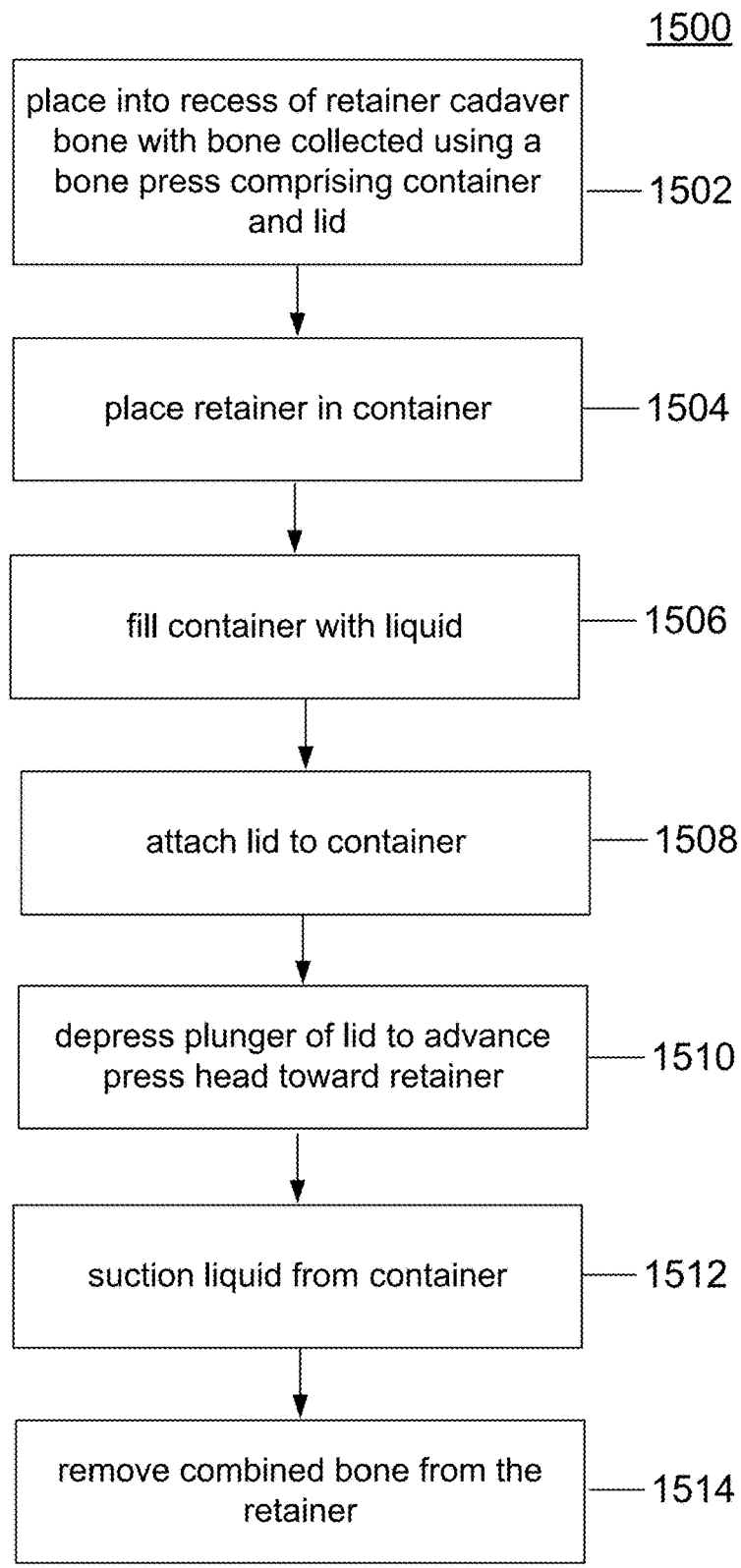
FIG. 15 illustrates another method in accordance with a preferred embodiment of the invention.

With reference to FIG. 15, another preferred method 1500 of preparing bone including cadaver bone for use in cervical fusion includes: (a) the step 1502 of placing into a recess of a retainer cadaver bone combined with a patient's bone collected using a bone press, the bone press comprising a container and a lid; (b) the step 1504 of placing the retainer in the container of the bone press; (c) the step 1506 of filling the container with a liquid; (d) the step 1508 of attaching the lid to the container; (e) the step 1510 of depressing a plunger of the lid such that a press head advances toward the retainer causing a dynamic pressure to act on the cadaver bone combined with the patient's bone; (0 the step 1512 of suctioning the liquid from the container; and (g) the step 1514 of removing the combined bone from the retainer for placement into a vertebral interspace of the patient.

Figure 16:
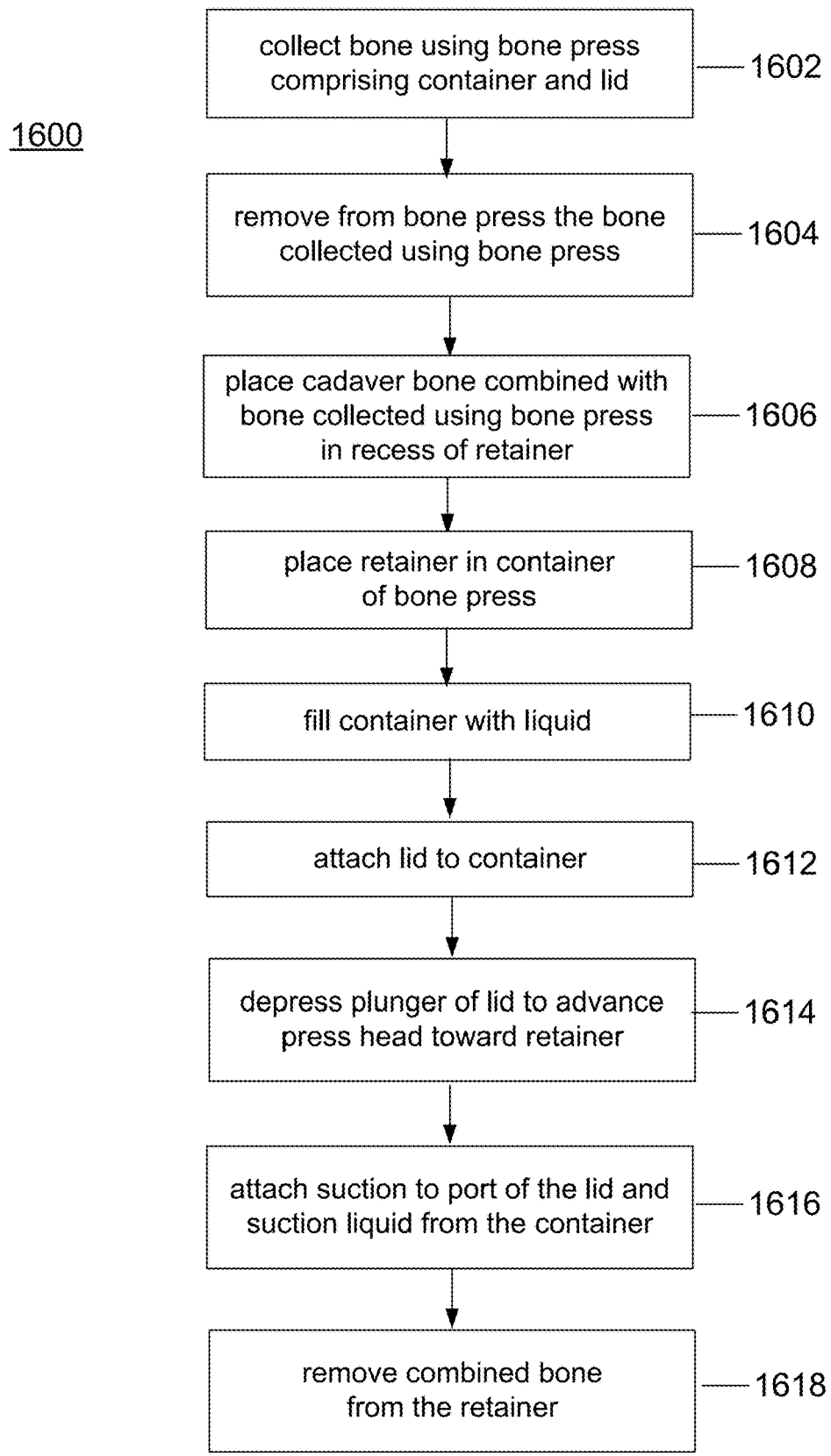
FIG. 16 illustrates another method in accordance with a preferred embodiment of the invention.

With reference to FIG. 16, another preferred method 1600 of preparing bone including cadaver bone for use in cervical fusion includes: (a) the step 1602 of collecting bone using a bone press, the bone press comprising a container and a lid; (b) the step 1604 of removing the bone collected using the bone press from the bone press; (c) the step 1606 of placing cadaver bone combined with the bone collected from the bone press into a recess of a retainer; (d) the step 1608 of placing the retainer in the container of the bone press; (e) the step 1610 of filling the container with a liquid; (f) the step 1612 of attaching the lid to the container; (g) the step 1614 of depressing a plunger of the lid such that a press head advances toward the retainer causing a dynamic pressure to act on the cadaver bone combined with the bone collected from the bone press; (h) the step 1616 of attaching suction to a port of the lid and suctioning the liquid from the container; and (i) the step 1618 of removing the combined bone from the retainer.

It is contemplated that the following would be instructions accompanying a preferred commercial kit in accordance with one or more embodiments of the present disclosure, wherein the kit would comprise a container, a lid including a plunger assembly, and a retainer. Moreover, as disclosed above, the kit further preferably comprises a bone press for recovery of bone from the patient in whom the bone graft will be placed. In this respect, a lid for collecting the aspirated fluid including the autologous bone in the container is included in the kit, together with an optional second container whereby collection can occur while pressing is performed in the other container. In other words, the bone press kit preferably includes the components of a kit of the incorporated references with the addition of a retainer as disclosed herein; however, a kit in accordance with one or more embodiments of the present disclosure may only include the subcomponents of the bone press, i.e., the container and lid with plunger assembly, combined with a retainer as disclosed herein.

The preferred instructions include: (1) Hold the cadaver bone graft in hand maintaining sterile conditions. (2) Take the staged autologous bone separated using a bone press or bone mill; using sterile technique, push the collected bone within the center conduit of the cadaver bone graft as tight as possible. (3) Take additional bone, as available, and push and lather the bone in a thick layer into and onto the superior and inferior surfaces of the cadaver bone graft. (4) Open the retainer and place on the sterile table. This can be done at the beginning of the surgery of just before use of the bone press, per preference of surgeon. (5) Holding retainer in hand, place the cadaver bone graft into the recess of the retainer after the cadaver bone graft has been prepared as described above. (6) Carefully place the retainer in the bottom of the empty container. (7) Fill the container with blood and/or saline liquid. The graft can be allowed to soak or sit in the mixture, or you can immediately proceed to pressing, per preference of surgeon. (8) Attach lid securely to the container, lining up ribs on container sides with ribs on sides of lid. (9) Attach suction to the side port of lid. (10) With steady downward pressure, depress plunger causing the press head to advance into abutment with retainer. Further depress plunger until press head abuts graft. The rubber retainer is resilient and compressible. (11) Repeat. (12) Tilt container toward suction port, allowing for adequate suction of fluid in container. (13) Remove lid and carefully tilt container, dropping retainer and/or graft gently on the sterile table. (14) Utilize graft as surgeon deems appropriate. (15) Repeat above steps if additional grafts are to be used. (16) To remove retainer from the bottom of the container, turn the container upside down on the sterile table and tap the bottom gently. The retainer should fall out. Use a blunt instrument to dislodge and remove, as needed.

In view of the foregoing, it will be understood that one or more embodiments of the present disclosure may very well provide a generally easy way to increase the number of bone cells that are infused into the bone matrix before placing a cadaver bone graft into an interbody space. The cadaver bone graft is widely accepted as a demineralized bone source requiring live bone cells for fusion to occur. It is well known that the cadaver bone graft cannot be placed into the vertebral interspace with fusion expectation without the infusion of stem cells, hip marrow aspirate, or live bone cells, which will allow for osteogenesis to occur. The use of the retainer allows for maximum infusion of live bone cells into the porous region of the cadaver graft during pressing, which is believed to optimize the graft for fusion after placement in the vertebral interspace. In this respect, it is believed that, as a result of the advancement of the press head toward the retainer, and the consequent increase in dynamic pressure exerted by the liquid on the cadaver bone graft, the infusion of bone cells into the cadaver bone is enhanced. Moreover, it is believed that the liquid in the container acts as a lubricant in carrying and dispersing the bone cells into and throughout the cadaver bone. It is further believed that use of the apparatus and methods of the present disclosure will decrease the reliance of obtaining a painful and expensive hip marrow aspirate, or otherwise harvesting bone from a remote harvest site. By not having to use the hip marrow aspirate, decreased morbidity will exist with less potential for infection at the remote harvest site. Avoidance of significant medical expenses also should be realized by not having to perform harvesting at a remote harvest site.

What is claimed is:

1. A bone infusion apparatus for interbody grafts, comprising:
   (a) a bone press, comprising:
      (i) a container, and
      (ii) a lid comprising,
         (A) a top having a suction port and configured for releasable attachment to the container in covering relation to a containment space of the container, and
         (B) a plunger comprising,
            (1) a shaft extending through and on opposite sides of the top between a distal end of the shaft and a proximal end of the shaft, and
            (2) a press head at the distal end of the shaft, the press head comprising a mesh screen defining openings therein extending between opposite sides of the press head; and
   (b) a retainer including a recess for receiving therein bone graft material, the retainer configured for removable disposition within the containment space of the container with the recess facing the press head when the lid is attached to the container, whereby manual operation of the plunger presses the press head into engagement with the retainer.

2. The apparatus of claim 1, wherein the retainer comprises a resilient and compressible material.

3. The apparatus of claim 1, wherein the recess of the retainer is located in a top surface of the retainer.

4. The apparatus of claim 3, wherein the press head is configured to abut the top surface of the retainer.

5. The apparatus of claim 1, wherein a profile of the retainer matches an inner surface profile of the containment space of the container.

6. The apparatus of claim 5, wherein the retainer is positionable within the container in a frictional fit and forms a fluid seal with an inner surface of the container.

7. The apparatus of claim 1, wherein the retainer consumes a bottom of the containment space of the container and forms an elevated floor of the containment space of the container when the retainer is disposed within the containment space of the container.

8. The apparatus of claim 1, wherein score lines or other areas of weakened integrity are provided in the retainer for increasing a perimeter of the recess; increasing a depth of the recess; or both.

9. The apparatus of claim 1, further comprising one or more spacers for consuming a bottom portion of a space within the recess of the retainer by which a depth of the recess of the retainer is adjusted.

10. The apparatus of claim 9, wherein a spacer of the one or more spacers has a profile that is the same as a profile of the recess, and wherein the spacer comprises rubber.

11. The apparatus of claim 1, wherein the retainer is disc-shaped shaped.

12. The apparatus of claim 1, wherein the press head is configured to abut bone graft material received within the recess of the retainer.

* * * * *